US009101557B2

(12) United States Patent
Cupp et al.

(10) Patent No.: US 9,101,557 B2
(45) Date of Patent: Aug. 11, 2015

(54) COMBINATION OF PROTEIN FORMS FOR HORNFLY VACCINATION

(75) Inventors: Mary S. Cupp, Owensboro, KY (US); Eddie W. Cupp, Owensboro, KY (US); Christine Navarre, Port Allen, LA (US); Dunhua Zhang, New Orleans, LA (US); Latora W. Todd Jackson, Montgomery, AL (US); Eugene Blair, Five Points, AL (US)

(73) Assignee: Auburn University, Auburn, AL (US)

( * ) Notice: Subject to any disclaimer, the term of this patent is extended or adjusted under 35 U.S.C. 154(b) by 341 days.

(21) Appl. No.: 13/438,263

(22) Filed: Apr. 3, 2012

(65) Prior Publication Data
US 2012/0263742 A1 Oct. 18, 2012

Related U.S. Application Data

(60) Provisional application No. 61/517,074, filed on Apr. 13, 2011.

(51) Int. Cl.
*A61K 39/00* (2006.01)
(52) U.S. Cl.
CPC .................. *A61K 39/0003* (2013.01)
(58) Field of Classification Search
None
See application file for complete search history.

(56) References Cited

U.S. PATENT DOCUMENTS

| | | | |
|---|---|---|---|
| 6,451,992 B1 * | 9/2002 | Cupp et al. | |
| 6,927,279 B2 * | 8/2005 | Cupp et al. | |
| 7,211,652 B2 | 5/2007 | Cupp et al | |
| 7,741,437 B2 * | 6/2010 | Valenzuela et al. | |

FOREIGN PATENT DOCUMENTS

| | | |
|---|---|---|
| AU | 694179 | 11/1995 |
| GB | 2327346 | 1/1999 |
| WO | WO 9504827 | 2/1995 |
| WO | WO 98/21324 | 5/1998 |
| WO | WO 98/40089 | 9/1998 |
| WO | WO 9902182 | 1/1999 |
| WO | WO 0011172 | 3/2000 |
| WO | WO 0109303 | 2/2001 |
| WO | WO 2005051996 | 6/2005 |

OTHER PUBLICATIONS

Cupp et al., Vaccine against horn flies could curb economic losses, NRI Res. Highlights, No. 3, Mar. 2002.*
Briegel, H., A.O. Lea, and M.J. Klowden. 1979. Hemoglobinometry as a method for measuring blood meal sizes of mosquitoes. J. Med. Entornol, : 15:235-238.
Cupp, E.W., M.S. Cupp, J.M.C. Ribeiro, and S.E. Kunz. 1998. Blood-feeding strategy of *Haematobia irritans* (Diptera: Muscidae). J. Med. Entomol. 35:591-595.
Cupp, M.S., D. Zhang, and E.W. Cupp. 2000. Horn fly saliva targets thrombin action in hemostasis. J Med Entomol. 37:416-421.
Cupp, M.S., E.W. Cupp, C. Navarre, N. Wisnewski, K.S. Brandt, G.M. Silver, D. Zhang, and V. Panangala. 2004. Evaluation of a recombinant salivary gland protein (thrombostasin) as a vaccine candidate to disrupt blood-feeding by horn flies. Vaccine. 22:2285-2297.
Cupp, M.S., E.W. Cupp, D. Zhang, X. Yue, L. Todd, V.Panangala, C.Navarre and E.Whitley. 2009. Salivary Gland Thrombostasin Isoforms Differentially Regulate Blood Uptake of Horn Flies Fed on New Zealand White Rabbits. J. Med. Entomol. 46(2):351-357.
Cupp, MS, EW Cupp, C Navarre, D Zhang, X Yue, L Todd, V Panangala. 2010. Salivary gland thrombostasin isoforms differentially regulate blood uptake of horn flies fed on control- and thrombostasin-vaccinated cattle. J. Med. Entomol. 47(4):610-617.
Derouen, S.M., J.E. Miller, L.D. Foil, G.T. Gentry. 2009. Control of horn flies (*Haematobia irritans*) and gastrointestinal parasites and its relation with cow-calf performance. Vet, Parasitol. 162 (3-4):320-326.
Guglielinone, A.A., E. Gimeno, J. Idiart, W.F. Fisher, M.M. Volpogni, 0. Qualm, O.S. Anziani, S.G. Flores, 0. Warnke. 1999. Skin lesions and cattle hide damage from *Haematobia irritans* infestations. Med. Vet. Entomol.13(3):324-329.
Hibler, C.P. 1966. Development of *Stephanofilaria stilesi* in the horn fly. J. Parasitol. 52(5):890-898.
Jensen, K.-M.V., J.B. Jespersen, M.A. Birkett, J.A. Pickett, G. Thomas, L.J. Wadhams and C. M. Woodcock. 2004. Variation in the load of the horn fly, *Haematobia irritans*, in cattle herds is determinded by the presence or absence of individual heifers. Med. Vet. Entomol. 18:275-280.
Kerlin, R.L., Allingham P. G., Acquired immune response of cattle exposed to buffalo fly (*Haematobia irritans exigua*), Vet. Parasitol. 1992; 143:115-129.
Owens, W.E., S.P. Oliver, RE: Gillespie, C.H. Ray and S.C. Nickerson. 1998. Role of horn flies (*Haematobia irritans*) in *Staphylococcus aureus*-induced mastitis in dairy heifers. Am. J. Vet. Res. 59:1122-1124.

(Continued)

*Primary Examiner* — Claire Kaufman
(74) *Attorney, Agent, or Firm* — Frost Brown Todd LLC

(57) ABSTRACT

Thrombostasin is an anti-clotting protein found in saliva of *Haematobia irritans*. Disclosed herein are studies testing blood uptake of horn flies feeding on cattle which confirm the association of ts genotype with blood uptake of horn flies. Blood uptake volumes of homozygous ts10 horn flies were lower than those of other ts genotypes when fed on control cattle. Cattle vaccinated with recombinant protein isoforms rTS9 or rTB8 resisted horn fly feeding by yielding lower blood volumes compared to flies feeding on control cattle. The impact of vaccination varied by ts genotype of flies. Cattle vaccinated with isoforms rTS9 resisted flies of ts2, ts9, and tb8 genotype. Vaccination with isoforms rTB8 produced resistance to ts8, ts9 and tb8 genotype flies. Horn flies of genotype ts10 were not affected with either TS isoforms and fed well on rTS9 and rTB9 vaccinated as on control-vaccinated cattle.

16 Claims, 3 Drawing Sheets

(56) References Cited

OTHER PUBLICATIONS

Owens, W.E., S.C. Nickerson and C.H. Ray. 2002. Effect of a pour-on and fly tag insecticide combination in controlling horn flies and *Staphylococcus aureus* mastitis in dairy heifers. 2002. J. Anim. Vet. Adv. 1(4):200-201.

Oyarzim, M.P., A. Quiroz and M.A. Birkett. 2008. Insecticide resistance in the horn fly: alternative control strategies. Med. Vet. Entomol. 22:188-202.

Pruett, J.H., C.D. Steelman, J.A. Miller, J.M. Pound and J.E. George. 2003. Distribution of horn flies on individual cows as a percentage of the total horn fly population. Vet.Parasitol. 116: 251-258.

Sanson, D.W., A.A. DeRosa, G.R. Oremus and L.D. Foil. 2003. Effect of horn fly and internal parasite control on growth of beef heifers. Vet. Parasitol. 117(4):291-300.

Steelman, C.D. 1976. Effect of external and internal arthropod parasites on domestic livestock production. Annu. Rev. Entomol, 21:155-178.

Untalan, P.M., J.H. Pruett, H.N. Atteberry, and C.D. Steelman. 2006. Thrombostasin isoform frequency in a Central Texas field population of the Horn Fly, *Haematobia irritans*. Vet. Parasitol. 142:359-366.

Zhang, D., M.S. Cupp, and E.W. Cupp. 2001. Polymorphism of Thrombostasin gene in the horn fly revealed in cDNA library and genomic DNA. Mol. Gen. Genom. 266:296-302.

Zhang, D., M.S. Cupp, and E.W. Cupp. 2002. Thrombostasin: Purification, molecular cloning, and expression of a novel antithrombin protein from horn fly saliva. Insect Biochem. Mal. Biol. 32:321-330.

Zhang D, MS Cupp, EW Cupp. 2004. Processing of pro-thrombostasin by a recombinant subtilisin-like proprotein convertase derived from the salivary glands of horn flies (*Haematobia irritans*). Ins Biochem Mol Biol. 34:1289-1295. Entomol.42: 805-811.

Perotti, M. A.; Lysyk, T. J.; Kalischuk-Tymensen, L. D.; Yanke, L. J.; Selinger, L. B. Growth and survival of immature *Haematobia irritans* (Diptera: Muscidae) is influenced by bacteria isolated from cattle manure and conspecific larvae. Journal of Medical Entomology (2001) vol. 38, No. 2, pp. 180-187, 18 refs. [Full Text].

Perotti M A; Lysyk T J. Novel growth media for rearing larval horn flies, *Haematobia irritans* (Diptera: Muscidae). Journal of medical entomology, (Jan. 2003) vol. 40, No. 1, pp. 22-29 [Full Text].

Allingham, P. G.; Leatch, G.; Kemp, D. H. An attempt to transmit *Anaplasma marginale* by buffalo flies (*Haematobia irritans exigua*). Australian Veterinary Journal (1994) vol. 71, No. 4, pp. 122-123.

Baron R W; Lysyk T J. Antibody responses in cattle infested with *Haematobia irritans irritans* (Diptera: Muscidae). Journal of medical entomology, (Sep. 1995) vol. 32, No. 5, pp. 630-5.

Bautista, Carlos R.; Giles, Isabel; Montenegro, Natividad; Figueroa, Julio V. (2004). Immunization of bovines with concealed antigens from*Haematobia irritans*. Annals of the New York Academy of Sciences, 1026, 284-288

Buxton B A; Hinkle N C; Schultz R D. Role of insects in the transmission of bovine leukosisvirus: potential for transmission by stable flies, hornflies, and tabanids. American journal of veterinary research, (Jan. 1985) vol. 46, No. 1, pp. 123-126. [Abstract Only].

Buxton, Bonnie Ann. The Role of Insects in the Transmission of Bovine Leukosis Virus. Dissertation Abstracts International, (1982) vol. 43, No. 10b, p. 3139. Order No. Aar8304982. 105 Pages. [Abstract Only].

Herms, W. B.; Wheeler, C. M.; Herms, H. P. Attempts to transmit equine encephalomyelitis by means of blood-sucking insects, especially mosquitoes. Jour Econ Ent, (1934) vol. 27, No. 5, pp. 987-998. [Abstract Only].

Lima, L. G. F.; Perri, S. H. V.; Prado, A. P. Evaluation of the biological action of simbovine insects in the horn fly (*Haematobia irritans*) (Diptera: Muscidae) production. Arquivos do Instituto Biologico (Sao Paulo) (2003) vol. 70, No. Suplemento 3, 144 p., 14 refs. ISSN: 0020-365 [Abstract Only].

Mochi, D. A.; Monteiro, A. C.; Machado, A. C. R.; Yoshida, L. Efficiency of entomopathogenic fungi in the control of eggs and larvae of the horn fly *Haematobia irritans* (Diptera: Muscidae). Veterinary Parasitology (2010) vol. 167, No. 1, pp. 62-66, 14 refs.

Muraleedharan, K.; Raghavan, R.; Murthy, G. V. K.; Murthy, V. S. S.; Swamy, K.G.; Prasanna, T. An investigation on the outbreaks of pox in buffaloes in Karnataka. Current Research—University of Agricultural Sciences (Bangalore) (1989) vol. 18, No. 2, pp. 26-27, 7 refs. [Abstract Only].

Okine, James Spencer. An immunological and olfactory study of horn flies, *Haematobia irritans* (L.): identification of antigens from the salivary glands and their relationships to host interaction. (1996) 129 pp. Avail.: Univ. Microfilms Int., Order No. DA9607114. Dissertation Abstracts International, (1994) vol. 56, No. 11B, p. 5905. Order No. AAI9607114. 129 pages. [Abstract Only].

Rivera B [Reprint Author]; Aycardi E R. Epidemiological Evaluation of External Parasites in Cattle from the Brazilian Cerrados and the Colombian Eastern Plains. Zentralblatt fuer Veterinaermedizin Reihe B, (1985) vol. 32, No. 6, pp. 417-424.

Tarry, D. W.; Bernal, L.; Edwards, S. Transmission of bovine virus diarrhoea virus by blood feeding flies. Veterinary Record (1991) vol. 128, No. 4, pp. 82-84, 17 refs. [Abstract Only].

Tolle A [Reprint author]; Reichmuth J; Franke V; Beimgraben J. Studies on Bovine Summer Mastitis. Kieler Milchwirtschaftliche Forschungsberichte, (1985) vol. 37, No. 2, pp. 125-212. [Abstract Only].

Torres, Lorena; Almazan, Consuelo; Ayllon, Nieves; Galindo, Ruth C; Rosario-Cruz, Rodrigo; Quiroz-Romero, Hector; de la Fuente, Jose. 2011. Functional genomics of the horn fly, *Haematobia irritans* (Linnaeus, 1758). BMC Genomics, (Feb. 10, 2011) vol. 12, pp. Article No. 105. ISSN: 1471-2164.

Wijffels, Gene; Hughes, Suzanne; Gough, Joanne; Allen, John; Don, Alistair; Marshall, Kay; Kay, Brian; Kemp, David. Peritrophins of adult dipteran ectoparasites and their evaluation as vaccine antigens. International Journal for Parasitology (1999), 29(9), 1363-1377.

Abebe, M., et al. "Anticoagulant Activity in Salivary Gland Extracts of Black Flies (Diptera: Simuliidae)," Journal of Medical Entomology, 1994, pp. 908-911, vol. 31(6), Entomological Society of America.

Byford et al., "A Review of Ectoparasites and Their Effect on Cattle Production," J. Anim Sci, 1992, pp. 597-602, vol. 70.

Cappello et al., "Isolation and Characterization of the Tsetse Thrombin Inhibitor: A Potent Antithrombotic Peptide from the Saliva of Glossina Morsitans," Am. J. Trop. Med. Hyg., 1996, pp. 475-480, vol. 54(5).

Cappello et al., "Erratum," American Journal of Tropical Medicine and Hygience, 1996, pp. 118, vol. 55(1).

Cross, M.L., et al., "Modulation of murine cellular immune responses and cytokines by salivary gland extract of the black fly *Simlium vittatum* (Diptera: Simuliidae)," Journal of Medical Entomology, 1993, pp. 928-935, vol. 30, No. 5.

Cross, et al., "Differential Modulation of Murine Cellular Immune Responses by Salivary Gland Extract of *Aedes aegypti*," Am. J. Trop. Med. Hyg., 1994, pp. 690-696, vol. 51(5).

Cupp, E.W. and Cupp, M.S., "Black Fly (Diptera: Simuliidae) Salivary Secretions: Importance in Vector Competence and Disease," Journal of Medical Entomology, 1997, pp. 87-94, vol. 34(2), Entomological Society of America.

Cupp, M.S., et al., "Analysis of cDNA and Recombinant Protein for a Potent Vasoactive Protein in Saliva of a Blood-feeding Black fly, Simulium Vittatum," The Journal of Experimental Biology, 1998, pp. 1553-1561, vol. 201, the company of Biologist Limited.

Cupp, et al., "Vasodilative Activity in Black Fly Salivary Glands," Am. J. Trop. Med. Hyg., 1994, pp. 241-246, vol. 50(2).

Harris et al., "Horn Flies and Stable Flies: Feeding Activity," Annals of the Entomological Society of America, 1974, pp. 891-894, vol. 67(6).

Hori, K., et al., "Digestive Enzymes in the Gut and Salivary Gland of the Adult Horn Fly *Haematobia irritans* (Diptera: Muscidae)," Appl. Ent. Zool., 1981, pp. 16-23, vol. 16(1).

Hudson, A., "Some Functions of the Salivary Glands of mosquitoes and other Blood-feeing Insects," Canadian Journal of Zoology, 1964, pp. 113-120, vol. 42.

Lewis et al., "Polynucleotide Vaccines in Animals: Enhancing and Modulating Responses," Vaccine, 1997, pp. 861-864, vol. 15, No. 8.

(56) References Cited

OTHER PUBLICATIONS

Qureshi et al., "Immunomodulatory Properties of Maxadilan, the Vasodilator Peptide from Sand Fly Salivary Gland Extracts," Am. J. Trop. Med. Hyg., 1996, pp. 665-671, vol. 54(6).

Ribeiro et al., "The Salivary Catechol Oxidase/Peroxidase Activities of the Mosquito *Anopheles albimanus*," J. Exp. Biol., 1993, pp. 273-287, vol. 179.

Ribiero, J.M.C., "Characterization of Vasodilator from the Salivary Glands of the Yellow Fever Mosquito *Aedes aegypti*," J. Exp. Biol., 1992, pp. 61-71, vol. 165.

Ribiero, J.M.C., "Role of Saliva in Blood-feeding by Arthopods," Ann. Rev. Entomol., 1987, pp. 463-478, vol. 32.

Schwinghammer et al., "Psyciological and Nutritional Response of Beef Steers to Infestations of the Horn Fly (Diptera: Muscidae)," Journal of Economic Entomology, 1986, pp. 1010-1014, vol. 79(4).

Tighe et al., "Gene Vaccination: Plasmid DNA Is More Than Just a Blueprint," Immunology Today, 1998, pp. 89-97, vol. 19, No. 2.

Vanhoorelbeke, K. et al., "Inhibition of Platelet Adhesion to Collagen as a New Target for Antithrombotic Drugs," Current Drug Targets—Cardiovascular & Haematological Disorders, 2003, pp. 125-140, vol. 3, Bentham Science Publishers Ltd.

\* cited by examiner

FIG 1.

N_tag_TB8
*MRGSHHHHHHGMASMTGGQQMGRDLYDDDDKDP*QNLVSGRRQHGAQGLSGY
SGDNDWGYYGEAGAPGSDYSGSSGQWAPLDFDYNSLPGLSGYNHEQQDYE
EDSYRHVRSAGPITLQLDDDDDDDSGIPIFEMDDEDIVIDSNDNQKFPLSFERE
PENEKNQIYIGLRARFNKFMAKFTSLFGRRRGVINIVPNAA (SEQ ID NO 11)

C_tag_TS9
*MA*QNVLSGRRQHGAQGLSGYSGDNDWGYYGEAGAPGSDYSGSSGQWAPLD
FDYNSLPGLSGYNHEQQDYEEDSYRHVRSAGPITLQLDDDDDDDSGIPIFEM
DDEDIEIDSNDNQKFPLSFEREPENEKNQIEIGLRARFNKFMAKFTSLFGRR
RGVIDIVPNAA*QLYTRASQPELAPEDPEDLEHHHHHHHHHH* (SEQ ID NO 12)

FIG 2.

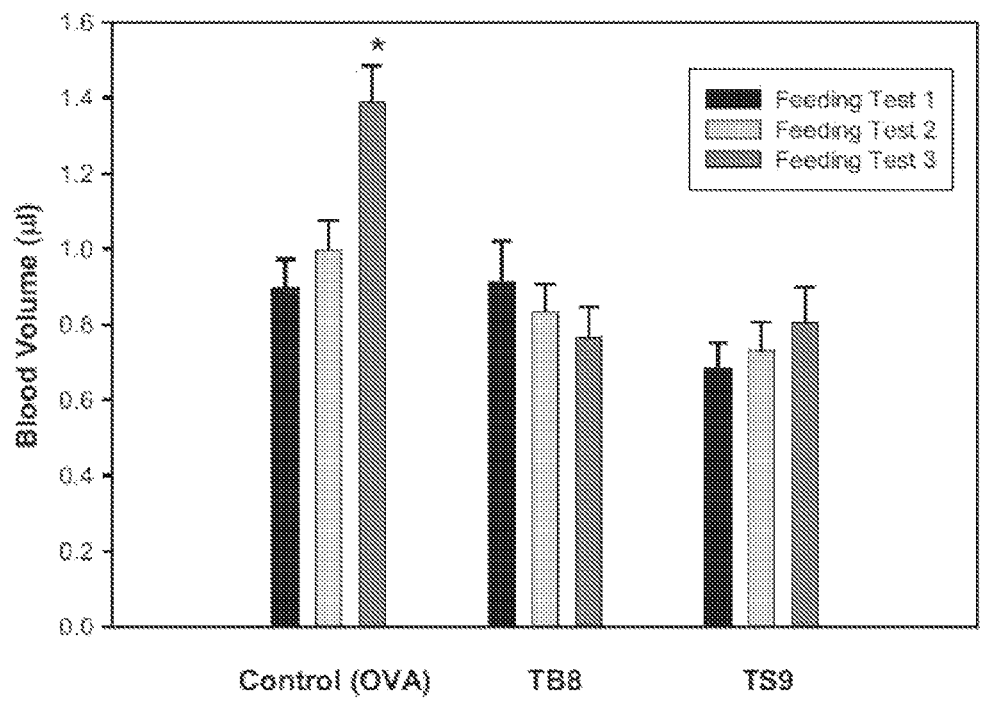

FIG 4.

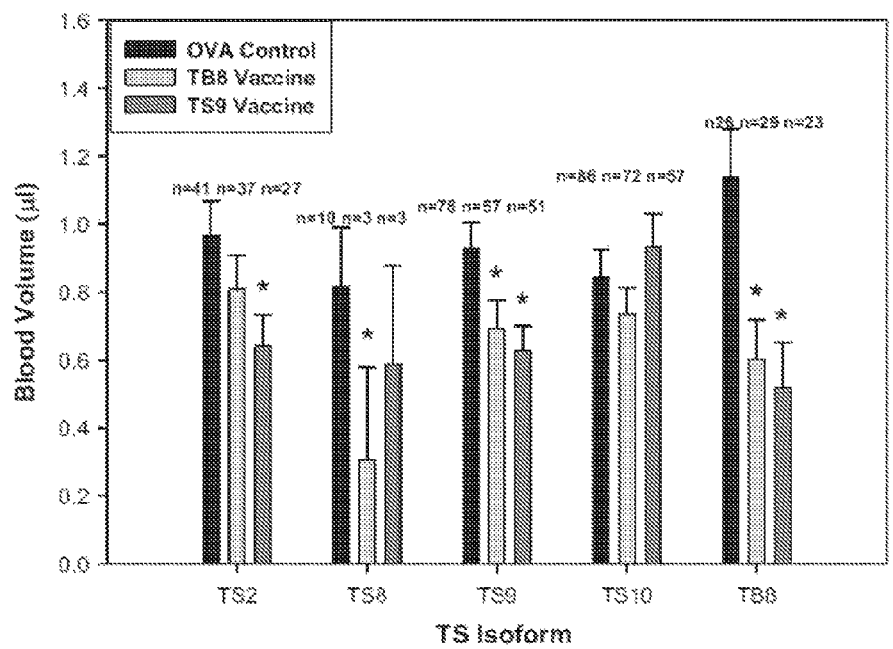

FIG 5.

```
        1                                                     50
TS-2    SAGPITLQLN  DDDDDDSGIP  IFEMDDEDED  SNDNQKFPLS  FERFPENEKN  (SEQ ID NO 1)
TS-8    SAGPITLQLD  DDDDDDSGIP  IFEMDDEDED  SNDNQKFPLS  FERFPENEKN  (SEQ ID NO 2)
TS-9    SAGPITLQLD  DDDDDDSGIP  IFEMDDEDED  SNDNQKFPLS  FERFPENEKN  (SEQ ID NO 3)
TS-10   SAGPITLQLD  DDDDDDSGIP  IFEMDDEDED  SNDNQKFPLS  FERFPENEKN  (SEQ ID NO 4)
TB-8    SAGPITLQLD  DDDDDDSGIP  IFEMDDEDVD  SNDNQKFPLS  FERFPENEKN  (SEQ ID NO 5)

51                         81
TS-2    QEGLRARFNK  FMAKFTSLFG  RRRGVDVPNA  A  (SEQ ID NO 6)
TS-8    QEGLRARFNK  FMAKFTSLFG  RRRSVDVPNA  A  (SEQ ID NO 7)
TS-9    QEELRARFNK  FMAKFTSLFG  RKRGVDVPNA  A  (SEQ ID NO 8)
TS-10   QVGLRARFNK  FMAKFTSLFG  RRRGVNVPNA  A  (SEQ ID NO 9)
TB-8    QVGLRARFNK  FMAKFTSLFG  RRRGVNVPNA  A  (SEQ ID NO 10)
```

COMBINATION OF PROTEIN FORMS FOR HORNFLY VACCINATION

CROSS REFERENCE TO RELATED APPLICATIONS

This application claims priority to U.S. Provisional Application Ser. No. 61/517,074 to Cupp et al., filed Apr. 13, 2011.

BACKGROUND OF THE INVENTION

Parasitism by blood-feeding horn flies, *Haematobia irritans* (L.), exacts a toll on cattle health and well being that results in economic losses estimated to approach $1 billion in North America alone (Cupp et al., 1998). In addition to the direct physiological impact of their feeding on cattle, horn flies are known to transmit the bovine filarial parasite, *Stephanofilaria stilesi* (Hibler, 1966) and the causative agent of bovine mastitis, *Staphylococcus aureus* (Owens et al., 2002, 1998). The benefits of horn fly control for promoting animal health and productivity have been demonstrated using presently available chemical means (Derouen et al., 2009, Sanson et al, 2003, Guglielmone et al., 1999).

Classical methods of chemical control, however, typically lead to selection for insecticide resistance that can severely limit the lifetime of any particular formulation. These complications of insecticidal use highlight the need to find other, more specific and long lasting, means of disrupting *H. irritans* parasitism of cattle (Oyarzim et al., 2008). Basic studies of horn fly blood-feeding revealed the importance of salivary proteins in fly-cattle interactions that lead to successful parasitism (Cupp et al., 1998). These studies identified a dominant thrombin-inhibiting protein, thrombostasin (TS), in horn fly saliva and implicated it as a key factor in successful blood-feeding by this important ectoparasite of cattle (Cupp et al., 2000).

Thus, there remains a need for agents capable of reducing the deleterious effect of the horn fly on susceptible populations.

BRIEF SUMMARY OF THE INVENTION

Disclosed herein are vaccine compositions that may comprise an isolated thrombostasin peptide or protein or a variant thereof and a pharmaceutically acceptable excipient, wherein said vaccine composition is capable of generating an immune response in a mammal to a horn fly thrombostasin protein. Also disclosed are methods for decreasing blood uptake from cattle by *Haemotobia irritans*, using a vaccine composition. Also disclosed are kits that may contain vaccine compositions as disclosed herein.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

This invention, as defined in the claims, can be better understood with reference to the following drawings. The drawings are for illustration purposes only, not for limitation.

FIG. 1. Recombinant horn fly salivary vaccine protein constructs. Amino acids shown in bold comprise the native salivary proteins while those in italics derive from the vector tag. Underlined amino acids identify the portion of thrombostasin that comprise the processed, active anti-thrombin portion of the two isoforms proteins. Amino acids enclosed in brackets identify the single amino acid variants of the isoforms.

FIG. 2. Blood uptake (mean±SEM) by horn flies fed on control or TS-vaccinated cattle in three sequential feeding tests).

FIG. 4. Relationship of blood uptake to ts genotype of horn flies when fed on control, rTB8 or rTS9-vaccinated cattle. Asterisk (*) indicates a significant effect of fly genotype on blood feeding from TS-vaccinated cattle compared to control cattle. ANOVA hypothesis test: ts2 genotype, vaccine TS9: $F=5.571$, $df=1$, $p=0.020$, $n=68$; ts8 genotype, vaccine TB8: $F=13.993$, $df=1$, $p=0.005$, n-13; ts9 genotype, vaccine TB8: $F-4.568$, $df=1$, $p=0.034$, $n=135$; vaccine TS9: $F=6.851$, $df=1$, $p=0.010$, $n=129$; tb8 genotype, vaccine TB8: $F=4.28$, $df=1$, $p41.031$, $n=55$; vaccine TS9: $F=10.598$, $df=1$, $p=0.002$, $n=49$.

FIG. 5. Amino acid composition of the thrombin inhibiting portion five major isoforms of Thrombostasin produced in saliva of horn flies collected from cattle in Alabama and Texas and from horn flies within a Texas colony. Amino acid variants are highlighted with bold lettering.

Figure 3:
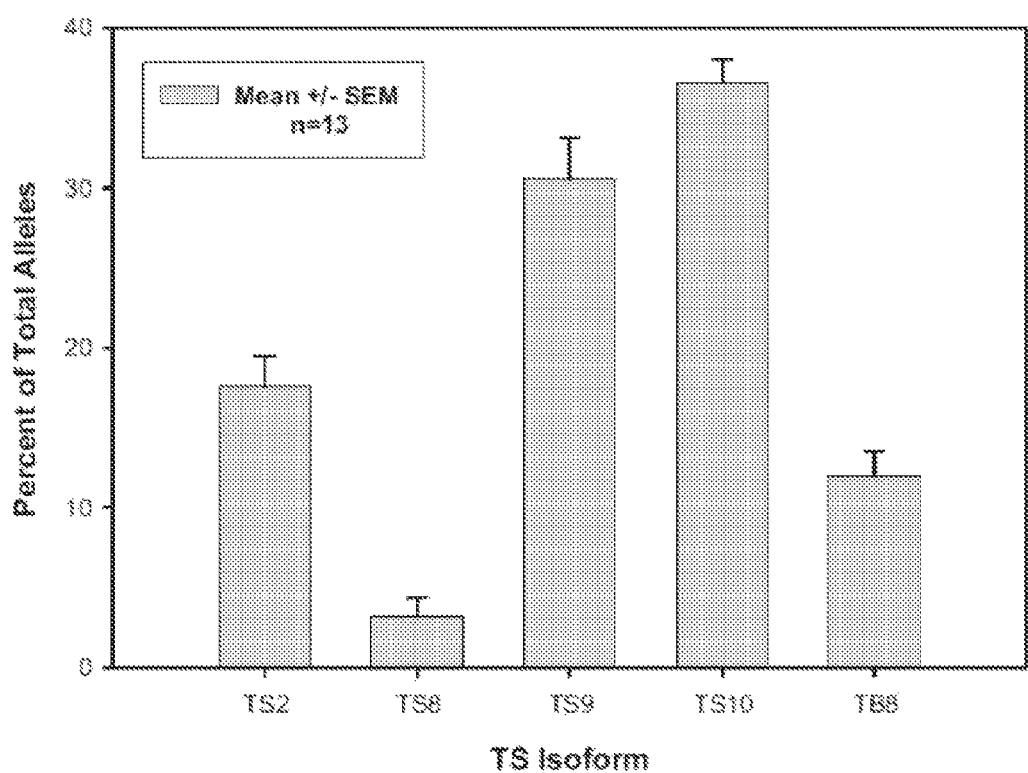
FIG. 3. Distribution of the five most common ts alleles (99%) of experimental flies used in feeding trials (mean±SEM; n=13 fly groups). Flies used for experiments were from a colonized strain. The distribution of alleles can vary somewhat among flies collected in the field from differing locations.

In the following description of the illustrated embodiments, references are made to the accompanying drawings, which form a part hereof, and in which is shown by way of illustration various embodiments in which the invention may be practiced. It is to be understood that other embodiments may be utilized and structural and functional changes may be made without departing from the scope of the present invention.

DETAILED DESCRIPTION OF THE INVENTION

Definitions

The following definitions are given to help the understanding of the present disclosure. The definitions given here are not exhaustive nor are they intended to be contradictory to the definitions as understood in the field or dictionary meaning. The definitions are given here to supplement or more clearly define the definitions known in the art.

Before the present compounds, compositions, articles, devices, and/or methods are disclosed and described, it is to be understood that this invention is not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Throughout this application, reference is made to various proteins and nucleic acids. It is understood that any names used for proteins or nucleic acids are art-recognized names, such that the reference to the name constitutes a disclosure of the molecule itself.

The articles "a", "an", and "the" as used herein in the specification and in the claims, unless clearly indicated to the contrary, should be understood to include the plural referents.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The term "adjuvant" is used herein to mean any molecule added to the vaccines described herein and may enhance antigenicity of the antigen described hereinafter.

The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). In some embodiments, individual substitutions, deletions or additions that alter, add or delete a single amino acid or a small percentage of amino acids can also be considered "conservative substitutions" if the change does not reduce the activity of the peptide (i.e. the ability of a protein or peptide variant to induce an immune response to the desired antigen).

As used herein, the term "effective amount" refers to an amount of vaccine which confers a therapeutic or prophylactic effect on the treated subject, at a reasonable benefit/risk ratio applicable to any medical treatment. In particular, the "effective amount" refers to an amount of a therapeutic composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. An effective amount may be administered in a dosing regimen that may comprise multiple unit doses. For any particular therapeutic agent, an effective amount (and/or an appropriate unit dose within an effective dosing regimen) may vary, for example, depending on route of administration, on combination with other pharmaceutical agents. Also, the specific effective amount (and/or unit dose) may depend upon a variety of factors the activity of the specific pharmaceutical agent employed; the specific composition employed; the age, body weight, general health, sex and diet of the recipient; the time of administration, route of administration, and/or rate of excretion or metabolism of the specific protein employed; the duration of the treatment; and like factors as is well known in the art.

The phrase "sequence homology" is used herein to refer to a comparison between amino acid or nucleic acid sequences. The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

As used herein, the term "percent sequence identity" or "percent identity" refers to the percentage of identical nucleotides or amino acids in a linear sequence of a reference ("query") molecule (or its complementary strand, in the case of nucleotides) as compared to a test ("subject") molecule (or its complementary strand, in the case of nucleotides) when the two sequences are optimally aligned (with, as applicable, appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package.RTM. (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more sequences may be to a full-length sequence or a portion thereof, or to a longer sequence. For purposes of this invention "percent identity" may also be determined using BLASTX version 2.0 for translated nucleotide sequences and BLASTN version 2.0 for polynucleotide sequences. In some embodiments, two sequences are considered to be substantially identical if the percent sequence identity is at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

The term "immune response" is used herein to mean the activation of a host's immune system, e.g., that of a mammal, in response to the introduction of an antigen. The immune response can be in the form of a cellular or humoral response, or both.

The term "step" may be used herein to connote different elements of methods employed, the terms should not be interpreted as implying any particular order among or between various steps herein disclosed unless and except when the order of individual steps is explicitly described.

As used herein, "percent (%) sequence identity" or "percent homology" when used in reference to a polynucleotide or to a polypeptide sequence is defined as the percentage of nucleotide or amino acid residues in a candidate sequence that are identical with the nucleotide or amino acid residues of a sequence disclosed herein. The percent identity shared by polynucleotide or polypeptide sequences is determined by direct comparison of the sequence information between the molecules by aligning the sequences and determining the identity by methods known in the art. In some embodiments, the alignment includes the introduction of gaps in the sequences to be aligned. In addition, for sequences which contain either more or fewer nucleotides or amino acids than those of the candidate polynucleotide or polypeptide sequences, it is understood that the percentage of homology will be determined based on the number of homologous nucleotides or amino acids in relation to the total number of nucleotides or amino acids. Thus, for example, homology of sequences shorter than those of the sequences identified herein will be determined using the number of nucleotides or amino acids in the shorter sequence.

As used herein, "variant" with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide). A "variant" of a peptide disclosed herein, for example SEQ ID NO:1 is meant to refer to a molecule substantially similar in structure and function, i.e. wherein the function is the ability to elicit an immune response to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical.

The practice of the present invention will employ, unless otherwise indicated, conventional techniques of molecular biology (including recombinant techniques), microbiology, cell biology and biochemistry, which are within the skill of the art.

DNA analyses of is genes in horn flies, collected from field populations and from a colonized strain, uncovered multiple point mutations at fixed positions (Zhang et al., 2001). Two mutations were "silent" whereas the remaining five specified peptides differ in molecular weight, isoelectric point and predicted secondary structure. Comparative analysis of the allelic mutations and their predicted effects on secondary structure of the active proteins suggested that evolutionary selection may be acting on the TS gene in response to one or more environmental pressures. This analysis implied that the selected changes in TS structure might enhance action of TS in thrombin inhibition and/or might diminish negative host immune responses that neutralize TS action (Zhang et al., 2001).

Recently published studies examined the possibility of a relationship between the volume of blood obtained by a horn fly when fed on a laboratory host, NZW rabbits, and the fly's gender or its ts genotype (Cupp et al., 2009). These studies found that blood uptake was not related to horn fly gender but was correlated with ts genotype. When physiologically similar flies of mixed gender and genotype were fed as a cohort on the same rabbits, blood volumes were diminished for those flies carrying even a single ts9 allele. In contrast, inheritance of one or both ts10 alleles was associated with increased blood feeding volumes. Neither the tb8 nor the ts2 alleles were associated with a significant impact on blood-feeding of NZW rabbits. Flies with the fifth most prominent ts allele (ts8) were too rare in the experimental population to provide meaningful analysis.

In studies reported here, we looked for similar relationships between a horn fly's ts genotype and blood feeding volumes obtained when fed on its natural host, cattle. These studies were part of a larger project investigating the effects of cattle vaccination against salivary TS on horn fly-cattle interactions. Control vaccinated cattle were used as a model to assess the impact of ts genotype on flies feeding on similar cattle (mixed breed dairy cattle, primarily Holstein) in the field. Cattle vaccinated with rTB8 or rTS9 were used to evaluate the potential of a TS vaccine to disrupt horn fly feeding and to assess any potential effects on vaccine efficacy corresponding to horn fly genotype.

The presence of a prominent blood clot-inhibiting protein in the saliva of both male and female horn flies implied a relevant, and perhaps essential, action in their blood feeding life style (Cupp et al., 1998). Experimental feeding studies supported the importance of salivary factors when blood meal volumes of horn flies increased if their hosts, NZW rabbits or cattle, had been sensitized to saliva by previous horn fly feeding (Cupp et al., 2004, 2009). That effect of host sensitization on blood uptake volumes was confirmed in the second cattle vaccine experiment described below Inhibition of the phenomenon by vaccination with two different rTS proteins strongly linked the feeding response to the TS component of horn fly saliva.

Because of the polymorphic nature of the ts gene, further analysis tested a potential relationship of feeding to each of the five most prominent ts alleles within the horn fly genome. A correlation was observed for horn flies fed on control NZW rabbits wherein differences in blood uptake among flies within a feeding group were linked to specific ts genotype (Cupp et al., 2009). In those studies, flies possessing one or more ts10 alleles obtained larger blood volumes after 20 min of feeding than did flies with one or more ts9 alleles. Although five major ts alleles have been identified in horn flies, those two alleles comprised 68% of the ts genes in the Kerrville, Tex. laboratory strain of horn flies that was used for experimental studies.

The reversal in outcomes for ts9 and ts10 genotype flies fed on cattle compared to rabbits was striking. In contrast to their superior feeding on a laboratory host, NZW rabbits, homozygous ts10 horn flies were less successful than the ts9 genotype in initial feedings on a natural host, dairy cattle. These differential effects highlight the potential importance of host-specific interactions with salivary TS in facilitating blood feeding of horn flies.

Sustained feeding of ts10 genotype flies tested on rTS9 immunized cattle, in contrast to the inhibited feeding of flies carrying ts2, ts9 and tb8 alleles, confirms a difference in cattle immune recognition of the TS10 protein isoform. This putative "escape" of ts10 genotype flies from an immune response to TS9 protein may account for the continued prevalence of this genotype in field populations, in spite of their sub-optimal feeding on cattle. Alleles for ts10 constituted 17% of the total ts genes within a collection of horn flies from dairy cattle in Alabama (Zhang et al., 2001) and 20% of ts10 alleles in flies collected from Camp Stanley, Tex. (Untalan et al., 2006) compared to ts9 alleles of 42% and 28%, respectively. Distribution of ts genotype horn flies did not appear to be uniform among cattle, however, when density on Texas field cattle was taken into account. Analysis of flies collected from cattle designated as low-carriers found that the number of flies carrying one or more ts10 alleles exceeded those with one or more ts9 alleles (25 flies with ts10 compared to 19 with ts9). The opposite relationship occurred on cattle designated as high-carriers of horn flies where 14 of 46 flies carried ts10 alleles (30%) compared to 25 with ts9 (65%; Untalan et al., 2006).

The concept of a particular horn fly infestation number on cattle that reaches an "economic threshold" is widely accepted (Steelman, 1976, Pruett et al., 2003, Jensen et al., 2004) and often is used to guide current methods of treatment. Cattle that carried high numbers of horn flies in one year were found to retain that status in the following year and the high levels of infestation were retained when individuals were moved to different herds (Jensen et al., 2004). Selection of cattle for resistance has been suggested as one means for keeping horn fly populations below the economic threshold (Pruett et al., 2003). In areas where ts9 genotype horn flies predominate in populations on high carrier cattle, as described in the TX study (Untalan et al., 2006), vaccination with rTS9 should provide a reasonably simple and effective method of reducing fly numbers by its impact on essential nutrition of the majority genotype.

Horn flies of ts2 genotype do not occur in high numbers among field-collected flies (Zhang et al., 2001, Untalan et al., 2006) but are more common in the Texas colony flies used for these feeding studies. The structure in the mature thrombin-inhibiting TS2 peptide varies from TS9 only at position 10, where an asparagine (N) replaces an aspartic acid (D) (FIG. 5). Both surface probability and antigenic index are predicted to be lower for TS2 peptide with the region affected extending from the leucine (L) at position 7 through the aspartic acid (D) at position 12. Although vaccination with rTS9 disrupted normal blood feeding by ts2 genotype flies, immunization with rTB8 was ineffective. This difference suggests that the substitution of an N for D at position 10 has significant effects on surface properties that masks an important epitope recognized by immune response to rTB8 vaccination. In addition to the three amino acid differences in the active thrombin-inhibiting peptides, rTB8 vaccine varied from rTS9 vaccine in the composition and location of the expression tags used for vaccine production (FIG. 1), which has the potential to affect surface properties and immune response.

In contrast to ts2, horn flies of ts8 genotype are prevalent within many field populations but occur in relatively low numbers within the Texas colony flies used for laboratory studies. Horn flies collected from dairy cattle in AL (mixed breed, primarily Holstein, Bos taurus) had ts8 alleles equal to ts10 (Zhang et al., 2001). Additionally, in three separate physical analyses of purified TS in saliva pools collected from horn flies obtained from the same herd, the quantity of peptide with molecular mass equal to TS8 was greater than that of TS10 and was exceeded only by peptide with mass equal to TS9 (unpublished observation; For one analysis, see FIG. 6, Zhang et al., 2002). The ts8 allele was well represented in field-collected horn flies of TX. In one location (Camp Stanley, Tex.) the ts8 allele made up 37.5% of the population and, in other collections, was a common allele among horn flies collected from low-carrier (24.5%) and high-carrier bulls (28.0%) (Untalan et al., 2006). Thus, an understanding of the feeding response of horn flies with ts8 genotype is of interest and is likely to be important in developing effective horn fly control that is based on targeting salivary proteins, especially in areas of ts8 genotype predominance.

The low frequency of the ts8 genotype within the TX colony horn flies and the lack of external markers for selecting specific genotypes limited the strength of conclusions about TS8 that could be drawn from these studies. Among the 438 flies (876 alleles) only 16 flies carried one or more ts8 alleles (n=28 alleles). Although the low numbers of ts8 flies observed in most groups warrant caution, analysis of variance detected higher blood uptake for homozygous ts8 flies than for those with only one ts8 allele. All heterozygous ts8 flies in these studies also carried ts9 alleles and would be expected to have sensitivity to TB8 or TS9 vaccination. Further studies of ts genes in field collected horn flies from a number of sites within the US, South America and Europe support the importance of TS8 peptide in horn fly saliva (unpublished observation).

In summary, these studies with a natural host (cattle), in addition to previous studies with a laboratory model host (rabbit), demonstrated a dynamic interaction between TS protein isoforms in horn fly saliva and a fly's ability to blood feed. Differences in response to TS isoforms between rabbit and cattle hosts indicate the importance of specific host factors to genetic selection of horn flies, including salivary TS. Immunization of Alabama dairy cattle with a recombinant form of the TS isoform most prevalent in local horn fly populations (rTS9) resulted in a significant decrease in blood uptake by flies carrying three of the five major ts alleles, ts2, ts9 and tb8. The lack of a significant impact of rTS9 vaccination on feeding of flies with ts10 or homozygous ts8 alleles indicates that a vaccine cocktail that includes rTS9 and one or both of those isoforms would be most successful for widespread control of this economically important ectoparasite.

In one aspect, a vaccine useful for preventing parasitism by *Haematobia irritans* is disclosed. The vaccine may be delivered to a mammal to modulate the activity of the mammal's immune system and thereby enhance the immune response. In one aspect, the vaccine composition may be capable of generating an immune response in a mammal to a horn fly thrombostasin protein. In one aspect, the mammal may be of the species *B. Taurus*.

The vaccine may comprise, in various aspects, thrombostasin proteins selected from those listed in Table 1.

TABLE 1

Amino Acid Sequences of the Five Major Isoforms of Thrombostasin contained in Horn Fly Saliva, Full Length and Thrombin Inhibiting Portion of the Full Length Protein.

| Isoform | Sequence | SEQ ID NO |
|---|---|---|
| ts2 (full length) | QNVLSGRRQHGAQGLSGYSGDNDWGYY GEAGAPGSDYSGSSGQWAPLDFDYNSLP GLSGYNHEQQDYEEDSYRHVRSAGPITL QLNDDDDDSGIPIFEMDDEDEDSNDNQ KFPLSFERFPENEKNQEGLRARFNKFMAK FTSLFGRRRGVDVPNAA | 1 |
| ts8 (full length) | QNVLSGRRQHGAQGLSGYSGDNDWGYY GEAGAPGSDYSGSSGQWAPLDFDYNSLP GLSGYNHEQQDYEEDSYRHVRSAGPITL QLDDDDDDDSGIPIFEMDDEDEDSNDNQ KFPLSFERFPENEKNQEGLRARFNKFMAK FTSLFGRRRSVDVPNAA | 2 |
| ts9 (full length) | QNVLSGRRQHGAQGLSGYSGDNDWGYY GEAGAPGSDYSGSSGQWAPLDFDYNSLP GLSGYNHEQQDYEEDSYRHVRSAGPITL QLDDDDDDDSGIPIFEMDDEDEDSNDNQ KFPLSFERFPENEKNQEGLRARFNKFMAK FTSLFGRRRGVDVPNAA | 3 |
| ts10 (full length) | QNVLSGRRQHGAQGLSGYSGDNDWGYY GEAGAPGSDYSGSSGQWAPLDFDYNSLP GLSGYNHEQQDYEEDSYRHVRSAGPITL QLDDDDDDDSGIPIFEMDDEDEDSNDNQ KFPLSFERFPENEKNQVGLRARFNKFMA KFTSLFGRRRGVNVPNAA | 4 |
| tb8 (full length) | QNLVSGRRQHGAQGLSGYSGDNDWGYY GEAGAPGSDYSGSSGQWAPLDFDYNSLP GLSGYNHEQQDYEEDSYRHVRSAGPITL QLDDDDDDDSGIPIFEMDDEDVDSNDNQ KFPLSFERFPENEKNQVGLRARFNKFMA KFTSLFGRRRGVNVPNAA | 5 |
| ts2 (thrombin inhibiting portion) | SAGPITLQLNDDDDDSGIPIFEMDDEDE DSNDNQKFPLSFERFPENEKNQEGLRARF NKFMAKFTSLFGRRRGVDVPNAA | 6 |
| ts8 (thrombin inhibiting portion) | SAGPITLQLDDDDDDDSGIPIFEMDDEDE DSNDNQKFPLSFERFPENEKNQEGLRARF NKFMAKFTSLFGRRRSVDVPNAA | 7 |
| ts9 (thrombin inhibiting portion) | SAGPITLQLDDDDDDDSGIPIFEMDDEDE DSNDNQKFPLSFERFPENEKNQEGLRARF NKFMAKFTSLFGRRRGVDVPNAA | 8 |
| ts10 (thrombin inhibiting portion) | SAGPITLQLDDDDDDDSGIPIFEMDDEDE DSNDNQKFPLSFERFPENEKNQVGLRARF NKFMAKFTSLFGRRRGVNVPNAA | 9 |
| tb8 (thrombin inhibiting portion) | SAGPITLQLDDDDDDDSGIPIFEMDDEDV DSNDNQKFPLSFERFPENEKNQVGLRARF NKFMAKFTSLFGRRRGVNVPNAA | 10 |

In one aspect, a vaccine composition comprising an isolated thrombostasin peptide or protein selected from SEQ ID NO 1 or a variant thereof; SEQ ID NO 2 or a variant thereof; SEQ ID NO 3 or a variant thereof; SEQ ID NO 4 or a variant thereof; SEQ ID NO 5 or a variant thereof; and a combination thereof, in combination with a pharmaceutically acceptable excipient, is disclosed.

In one aspect, a composition comprising one or more peptides or proteins selected from a peptide or protein having at least about 80% sequence identity to SEQ ID NO 1, a peptide or protein having at least about 80% sequence identity to SEQ ID NO 2, a peptide or protein having at least about 80% sequence identity to SEQ ID NO 3, a peptide or protein having at least about 80% sequence identity to SEQ ID NO 4, a peptide or protein having at least about 80% sequence identity to SEQ ID NO 5, and a combination thereof with a pharmaceutically acceptable excipient, is disclosed.

In one aspect, the composition may comprise SEQ ID NO 2 or a variant thereof, SEQ ID NO 3 or a variant thereof, and SEQ ID NO 4 or a variant thereof. In one aspect, the composition comprising SEQ ID NO 2, SEQ ID NO 3, and SEQ ID NO 4 may further comprise SEQ ID NO 5 or a variant thereof.

In one aspect, the composition may comprise SEQ ID NO 1 or a variant thereof, SEQ ID NO 2 or a variant thereof, and SEQ ID NO 4 or a variant thereof.

In one aspect, the composition may comprise SEQ ID NO 2 or a variant thereof.

In one aspect, the composition may comprise SEQ ID NO 3 or a variant thereof.

In one aspect, the composition may comprise SEQ ID NO 4 or a variant thereof.

In one aspect, the composition may comprise SEQ ID NO 5 or a variant thereof.

In one aspect, the composition may comprise SEQ ID NO 2 or a variant thereof, SEQ ID NO 3 or a variant thereof, SEQ ID NO 5 or a variant thereof.

In one aspect, the composition may comprise any of the combinations set forth above, wherein the composition further comprises SEQ ID NO 1.

In another aspect, a vaccine composition comprising an isolated thrombostasin peptide or protein selected from SEQ ID NO 6 or a variant thereof; SEQ ID NO 7 or a variant thereof; SEQ ID NO 8 or a variant thereof; SEQ ID NO 9 or a variant thereof; SEQ ID NO 10 or a variant thereof; and a combination thereof; and a pharmaceutically acceptable excipient, is disclosed.

In one aspect, a composition comprising a peptide or protein selected from a peptide or protein having at least about 80% sequence identity to SEQ ID NO 6 or a variant thereof, a peptide or protein having at least about 80% sequence identity to SEQ ID NO 7 or a variant thereof, a peptide or protein having at least about 80% sequence identity to SEQ ID NO 8 or a variant thereof, a peptide or protein having at least about 80% sequence identity to SEQ ID NO 9 or a variant thereof, a peptide or protein having at least about 80% sequence identity to SEQ ID NO 10 or a variant thereof, and a combination thereof, is disclosed.

In one aspect, the composition may comprise SEQ ID NO 8 or a variant thereof, SEQ ID NO 7 or a variant thereof, and SEQ ID NO 9 or a variant thereof. In this aspect, the composition may further comprise SEQ ID NO 10 or a variant thereof.

In one aspect, any of the composition disclosed herein, may be capable of generating an immune response in a mammal to a horn fly thrombostasin protein.

In one aspect, any of the one or more said peptide or proteins described herein may further comprise an immunogenic sequence. The immunogenic sequence may comprise an amino acid sequence. The immunogenic sequence may be operatively connected to the peptide or protein of the compositions described herein, such as in the case of portions of a plasmid vehicle used during construction of the vaccine. In one aspect, the immunogenic sequence may comprise a sequence selected from an amino acid sequence comprising from about 10 to about 500 amino acids, or from about 25 to about 400 amino acids, or from about 40 to about 300 amino acids, or from about 50 to about 200 amino acids. In some aspects, the immunogenic sequence may be sufficient to eliminate the need for an adjuvant. In this aspect, the composition does not comprise an adjuvant.

Pharmaceutically acceptable excipients may include functional molecules as vehicles, adjuvants, carriers or diluents, which are known in the art and readily available to the public.

In one aspect, the excipient may comprise an adjuvant. Suitable adjuvants may include, mineral gels, e.g., aluminum hydroxide; surface active substances such as lysolecithin; glycosides, e.g., saponin and saponin derivatives such as Quil A or GPI-0100; cationic surfactants, e.g. DDA (quaternary hydrocarbon ammonium halogenides, pluronic polyols; polyanions and polyatomic ions; polyacrylic acids, non-ionic block polymers, e.g., Pluronic F-127 (BASF., USA); Avridine and Rantidine; peptides; recombinant mutant labile toxins, e.g., leukotoxin (LT) or cholera toxin (CT); chemically bound or close proximity molecular transporters; mineral oils, e.g. Montanide ISA-50 (Seppic, Paris, France), carbopol, Amphigen (Hydronics, USA), Omaha, Nebr. USA, Alhydrogel, (Superfos Biosector, Frederikssund, Denmark) oil emulsions, e.g. an emulsion of mineral oil such as BayolF/Arlacel A and water, or an emulsion of vegetable oil, water and an emulsifier such as lecithin; alum, cholesterol cytokines and combinations of adjuvants. Polyatomic ions can also function as dispersing, thickening and anticaking agents which allow the vaccine to be resuspended as a mondisperse suspension after a prolonged period of settling. The adjuvant combinations may be presented in aqueous, encapsulated (controlled or delayed release) or microencapsulated forms.

In one aspect, the vaccine composition may comprise a preservative. Suitable preservatives may include benzalkonium chloride (0.003-0.03% w/v); chlorobutanol (0.3-0.9% w/v); parabens (0.01-0.25% w/v) and thimerosal (0.004-0.02% w/v).

The compositions may be formulated according to the mode of administration to be used. In cases where pharmaceutical compositions are injectable pharmaceutical compositions, they are sterile, pyrogen free and particulate free. An isotonic formulation may be used. Additives for isotonicity may include sodium chloride, dextrose, mannitol, sorbitol and lactose. In some cases, isotonic solutions such as phosphate buffered saline may be preferred. Stabilizers may include gelatin and albumin. In some aspects, a vasoconstriction agent may be added to the formulation. In some aspects, a stabilizing agent that allows the formulation to be stable at room or ambient temperature for extended periods of time, such as LGS or other polycations or polyanions may be added to the formulation.

In another aspect, a method for decreasing blood uptake from a mammal, in one aspect, cattle, by *Haematobia irritans* is disclosed. In this aspect, the method may comprise the step of vaccinating a mammal with a composition as described herein. In one aspect, the vaccination step may comprise more than one administration of the vaccine composition. The administration step may occur intramuscularly, intraparitoneally, intraarterially, intraoccularly, parenterally, orally, intranasally, oronasally, or transdermally. The composition may be administered by means including traditional syringes, needleless injection devices, or other physical methods such as electroporation ("EP"), "hydrodynamic method", or ultrasound.

In some aspects, the mammal may be vaccinated at a plurality of injection sites, and at a plurality of times. In one aspect, the administration step may be administered prophylactically, therapeutically, or in some aspects, both prophylactically and therapeutically. The mammal may be of the species *B. Taurus*.

In another aspect, a kit for providing improved resistance to *Haematobia irritans* blood uptake in cattle is disclosed, wherein the kit may comprise a vaccine composition as disclosed herein.

In one aspect, a kit is disclosed. The kit may comprise at least two vaccine compositions for multiple administrations. In other aspects, the kit may comprise a vaccine composition provided in a pre-dosed delivery device.

EXAMPLES

Materials and Methods

Data for the horn fly blood-feeding and genotype analyses presented here were gathered as part of two cattle vaccine trials conducted two years apart in 2002 and 2004. Cattle were vaccinated with OVA (control) or rTB8 proteins in the first trial and with OVA (control), rTB8 or rTS9 proteins in the second trial. Overall blood feeding results of the 2002 trial were presented previously (Cupp et al., 2004) and similar results for the 2004 trial are contained in this report. A subset of flies from the two trials was analyzed further for specific is genotype (438 of 798 total flies) and tested for association with blood-feeding success.

Preparation of vaccine antigens. Preparation of rTB8, the first recombinant isoform produced for a vaccination trial, was described previously (Cupp et al., 2004). SDS/PAGE analysis of rTB8 showed that, following expression in *E. coli* and purification, five related peptides were recovered with the most abundant peptide lacking 41 amino acids from the C' terminus (Cupp et al., 2004). All recovered rTB8 peptides, including a full-length peptide, were combined for the vaccine, which was subsequently labeled "TSPool". The same rTB8 protein used in that vaccine trial was used in the second trial conducted in 2004.

An additional isoform, rTS9, was prepared for use in the second trial to compare efficacy with rTB8. Recombinant TS9 (rTS9) vaccine was prepared from a cDNA isolated from a horn fly salivary gland library (Zhang et al, 2001) after subcloning into the pTriEx-4 vector (Novagen) for expression in *E. coli* Rosseta strain host cells. The rTS9 fusion protein, with a purification tag at the C' terminus, was extracted from the soluble fraction and purified with a HIS-binding resin (His.Bind®—Novagen). Recombinant TS9 was purified further with RP/HPLC. Analysis by SD S-PAGE and western blotting showed a peptide pool, similar to rTB8 which was more than 95% pure (data not shown). Endotoxin was removed from the newly prepared vaccine using EndoTrap® Blue (Boca Scientific, Boca Raton, Fla.) according to manufacturer's instructions.

Amino acid composition of the two recombinant TS proteins used for vaccination are shown in FIG. 1. The three sites where amino acid variants occur in the active, mature antithrombin proteins are enclosed in brackets. Vaccine protein constructs also differed in the location of vector-added elements (identified by italics), including a HIS purification tag, which were located on the N' terminus for rTB8 and on the C' terminus for TS9 (FIG. 1). The rTB8 vaccine corresponds to SEQ ID NO 11; the rTS9 vaccine corresponds to SEQ ID NO 12.

Cattle Host. Housing and vaccination of horn fly-naïve, mixed-breed male dairy calves has been described in detail for one of the two cattle vaccine trials providing data for this report (Cupp et al., 2004). Calf characteristics, housing and vaccination procedures were similar for the second trial and are described in brief below. All animal-related protocols were approved by the AU Institutional Animal Care and Use committee.

Immunization. Six calves were tested in vaccine trial #1 and twelve were used for trial #2. For both experiments, calves were born in winter when no adult horn fly exposure would occur, age-matched and placed in groups for immunization and testing. Details of trial 1, with three groups of rTB8 or OVA (control)-immunized calves, have been reported previously (Cupp et al., 2004). For the second trial, twelve calves were placed into one of four groups of three. One calf within each group was immunized with OVA (control), rTB8 or rTS9 antigen proteins using the regimen shown in Table 2. Blood uptake trials were conducted for calves from all four groups, whereas is genotype was determined for flies exposed to calves in Groups 1 and 2.

TABLE 2

Immunization Schedule of Second Vaccine Trial

| Cattle Group | Prime | Boost 1 | Boost 2 | Boost 3 |
|---|---|---|---|---|
| 1 | Day 0 | Day 14 | Day 35 | — |
| 2 | Day 0 | Day 14 | Day 35 | Day 108 |
| 3 | Day 0 | Day 14 | Day 35 | Day 77 |
| 4 | Day 0 | Day 14 | Day 62 | — |

Vaccine emulsions were formed with 50 µg of antigen protein in Freund's Complete Adjuvant (FCA) for the priming dose and with Freund's Incomplete Adjuvant (FIA) for the boosts. The priming dose was sub-divided into 4 portions which were injected intradermally (ID) and subcutaneously (SQ). Boosting injections were all SQ. Immunizations were administered and testing of cattle was conducted by group to avoid any unpredictable environmental bias for a specific treatment.

Host response to immunization. Extent and specificity of serum antibody response of individual cattle were measured by ELISA to confirm an active immune response. Microtiter wells were coated with 5 µg test protein and antibody binding from sera diluted 500 to 512.000-fold was tested. Detection of specific binding utilized peroxidase-labeled goat anti-bovine IgG and TMB peroxidase substrate (K&P Laboratories, Gaithersburg, Md.), with color intensity measured by absorption at 450 nm. Additional effects of vaccination on calf cellular immune response and fly reproduction have been described for trial #1 (Cupp et al., 2004).

Horn Flies. Horn fly pupae were shipped overnight from a colony maintained by the USDA Livestock Insects Laboratory in Kerrville, Tex. Immediately upon arrival, they were stored at 4° C. to attenuate further development until needed for experimental use, For adult development, pupae were gently mixed for uniformity before a portion was transferred to an open petri dish within an emergence cage (constructed from a cardboard ice cream carton), and placed in an insect incubator at 28° C. with a photoperiod of 16:8 (L:D) h. A water-soaked cotton ball, placed on the top screen of the cage, provided moisture during emergence of metabolically similar adult flies of either sex.

Blood Uptake Studies. Blood uptake of horn flies from control and TS-vaccinated calves was assessed using quantitative measurement of individual blood-meals. A feeding cage (7.5 cm in diameter×1.5 cm deep) was secured to the hide on the back of the calf by three sutures. Twenty flies representing a mixture of sexes were added to the pre-attached cage and allowed to feed for exactly 20 minutes before the sutures were clipped and the cage was removed from the calfs back. Blood digestion was inhibited by placing the feeding cage with flies in a cooler on a layer of paper towels underlain with crushed ice. Individually dissected mid-guts were added to an aliquot of Drabkins reagent which forms a cyanide-hemoglobin complex that absorbs light of 540 nm wavelength (Briegel and Klowden, 1979). Blood volumes were determined from a standard curve prepared from cattle host blood which was drawn immediately after fly feeding (Cupp et al., 2004).

Genomic Analyses. A randomly selected subset of frozen carcasses of flies previously evaluated for blood feeding on Control or TB8 vaccinated calves (Cupp et al., 2004) were analyzed for is genotype as part of the data set for this report. Additionally, a subset of horn flies from the second TS vaccination study, conducted in 2004 and described above, were evaluated to provide the remaining observations. From a total of 798 horn flies evaluated for blood uptake in those two studies, a total of 438 were evaluated further for is genotype and comprise the data set.

Immediately after blood-meal removal, the fly carcass was placed in 500 µl of absolute ethanol and frozen at −70° C. for subsequent DNA extraction. Total genomic DNA of individual horn flies was extracted using a method described previously (Zhang et al. 2001). In brief, individual flies were homogenized with 40 µl of buffer (10 mM Tris-HCl, pH 8.0, 2 mM EDTA, and 0.4M NaCl), and total DNA was extracted from the homogenate. Ten to 50 nanograms of DNA was used from each fly for polymerase chain reaction (PCR) with Tag DNA polymerase. The following primer pairs were used: HITS8 (5-_ATCATGAAGCATTTCGTAG-3_), corresponding to SEQ ID NO 13 and HITS18 (5_-GCT TAT GCA GCA TTG GGA ACA-3_) corresponding to SEQ ID NO 14. The PCR was carried out by mixing the following components in a final volume of 50 µl: 20 mM Tris-HCl, pH 8.4, 50 mM KCl, 1.5 mM MgCl$_2$, 200 µl dNTPs, and 0.2 µM of each primer and genomic DNA. The mixture was incubated at 94° C. for 3 min and then maintained at 80° C. until 2.5 U of polymerase was added to each reaction. Amplification for 35 cycles was followed: 94° C. for 45 s, 60° C. for 45 s, and 72° C. for 80 s. A final extension step was carried out at 72° C. for 7 min. Amplification products were directly sequenced after separation by agarose gel and purification with Sephaglas BP (Pharmacia Biotech). Sequencing chromatograms and digital readout files of the amplification products were generated by the Auburn University Genetics Analysis Laboratory. Further nucleotide and amino acid analyses were carried out using the Vector NTI program version 9. TS gene allele assignment was performed as described previously (Zhang et al. 2001).

Statistical Analysis. Data were evaluated using Systat Software, version 11.0.0.1 (Systat Software, Inc., San Jose, Calif.).

Results

Calves responded to immunization with an increase in specific antibody to their vaccine antigen (Table 3, column 2). OVA-immunized (control) cattle showed serum antibody recognition of OVA (Table 3, row 2, column 2) but only background response to rTB8 (Table 3, row 2, column 3) or rTS9 (Table 3, row 2, column 4). TB8-immunized calves had serum antibody that bound rTB8 protein two-fold greater than rTS9 (Table 3, row 3, columns 3 and 4) whereas antibody generated in TS9-immunized calves bound rTS9 and rTB8 equally well (Table 3, row 4, columns 3 and 4).

TABLE 3

Antibody response measured by ELISA (serum dilution of 1/1000)

| Sera from calf Vaccinated with | OD 450 (Vaccine Ag) | OD 450 (Test TB8) | OD 450 (Test TS9) |
|---|---|---|---|
| OVA | 0.49 ± 0.28 | 0.13 ± 0.03 | 0.06 ± 0.02 |
| TB8 | 0.64 ± 0.31 | 0.50 ± 0.08 | 0.27 ± 0.11 |
| TS9 | 0.59 ± 0.17 | 0.67 ± 0.21 | 0.61 ± 0.32 |

From the set of all flies evaluated for blood uptake (n=798) all flies from experiment 1 and a subset of flies from experiment 2, (Table 2, Groups 1 and 2), were further analyzed for is genotype (n=438). Differences in mean blood uptake due to treatments which were observed in the parent group, (ANOVA: F=6.957, P=0.001; n=798) were detected similarly in this subset (ANOVA: F=5.108, P=0.006; n=438). Additionally, blood uptake of specific treatment groups did not differ between the two vaccine trials (Table 4; ANOVA: F=0.100, P=0.785; n=26), allowing the two data sets to be combined for testing isoform effects.

The increased uptake of blood by horn flies feeding on control cattle after sensitization by prior horn fly biting, as reported earlier (Cupp et al., 2004), was confirmed in the second trial (FIG. 2; ANOVA: F=5.230, P=0.023, n=642). When cattle were vaccinated with rTB8 or rTS9 however, no increase in blood uptake occurred (FIG. 2).

Further analysis of blood uptake by specific genotype revealed a differential effect of ts alleles on feeding success. Ninety-nine percent of all thrombostasin genes within the experimental horn fly population were composed of five ts alleles, ts2, ts8, ts9, ts10 and tb8, with ts9 and ts10 accounting for 67% of the total (FIG. 3). Although the mean blood uptake of the total population of flies was decreased when flies fed on cattle vaccinated with rTB8, the effect was due to an impact only on flies with ts8, ts9 and tb8 alleles (FIG. 4), which together comprised 46% of the population (FIG. 3). In addition to flies carrying ts9 and tb8 alleles, flies with ts2 alleles (17%), but not those with ts8, were inhibited in feeding from cattle when rTS9 was used as the vaccination protein (FIG. 4). In contrast, flies carrying ts10 alleles (36%) were as successful in feeding from TB8 or TS9-vaccinated calves as from controls (FIG. 4).

TABLE 4

Blood Uptake by Flies Feeding on Experimental Calves.
Blood uptake was decreased for flies fed on TB8 or TS9-immunized cattle for the set of All Flies (ANOVA: F = 6.957, P = 0.001; n = 798) and for the Genotype subset (ANOVA: F = 5.108, P = 0.006; n = 438). Mean blood volumes for treatment groups were not different between the set of all flies and the Genotype subset (ANOVA: F = 0.100, P = 0.755; n = 26).

| Vaccine | Set of all flies Mean ± SEM (n =) | Genotype subset Mean 1 SEM (n=) |
|---|---|---|
| OVA (control) | 0.95 ± 0.04 (304) | 0.90 ± 0.05 (178) |
| TB8 | 0.79 ± 0.04 (275) | 0.71 ± 0.05 (144) |
| TS9 | 0.73 ± 0.05 (219) | 0.73 ± 0.06 (116) |

Data in Tables 5-10 show blood uptake when flies were homozygous or heterozygous for specific is gene alleles. Blood volumes obtained from TS-vaccinated calves were similar for both homozygous and heterozygous flies carrying alleles ts2 (Table 5), ts9 (Table 6), and tb8 (Table 7). Sorting of feeding data by number of ts8 alleles (Table 8) emphasized the very low frequency of this genotype in the colony horn fly population used for experimental studies, ANOVA, however, detected an increase in blood uptake for ts8 homozygous flies compared to flies with a single ts8 allele (ANOVA: F=19.314, P=0.002, n=16). A similar analysis of horn flies with ts10 alleles uncovered a significant decrease in blood uptake from control-vaccinated cattle when both genes were ts10 (Table 9; ANOVA: F=4.190, P=0.044, n=86). Feeding of ts10 flies on control-vaccinated calves was explored further by sorting data by feeding times. This analysis revealed that lower blood uptake of ts10 homozygous flies from control cattle occurred only for the first two feedings. But after extensive field exposure of cattle to horn flies that occurred following the second feeding test, blood meal volumes of ts10 genotype flies reached that of other genotypes in the third feeding test (Table 10).

TABLE 5

Flies with ts2 Alleles. Blood uptake did not differ between heterozygous and homozygous ts2 flies
(ANOVA: F = 0.060, P = 0.807, n = 105).

| | Vaccine: OVA (Control) | Vaccine: TB8 | Vaccine: TS9 |
|---|---|---|---|
| 1 allele | n = 26 | n = 25 | n = 12 |
| | 0.983 ± 0.130 | 0.847 ± 0.122 | 0.578 ± 0.112 |
| 2 alleles | n = 15 | n = 12 | n-15 |
| | 0.935 ± 0.171 | 0.727 ± 0.180 | 0.691 ± 0.139 |

TABLE 6

Flies with ts9 Alleles. Blood uptake did not differ between heterozygous and homozygous ts9 flies
(ANOVA: F = 0.020, P = 0.888, n = 186).

| | Vaccine: OVA (Control) | Vaccine: TB8 | Vaccine: TS9 |
|---|---|---|---|
| 1 allele | n = 39 | n = 27 | n-33 |
| | 0.959 ± 0.110 | 0.623 ± 0.120 | 0.678 ± 0.095 |
| 2 alleles | n = 39 | n = 30 | n = 18 |
| | 0.898 ± 0.105 | 0.757 ± 0.114 | 0.533 ± 0.114 |

TABLE 7

Flies with tb8 Alleles. Blood uptake did not differ between heterozygous and homozygous tb8 flies
(ANOVA: F = 1.678, P = 0.199, n = 78.

| | Vaccine: OVA (Control) | Vaccine: TB8 | Vaccine: TS9 |
|---|---|---|---|
| 1 allele | n = 19 | n = 19 | n = 18 |
| | 1.257 ± 0.173 | 0.609 ± 0.142 | 0.546 ± 0.164 |
| 2 alleles | n = 7 | n = 10 | n = 5 |
| | 0.816 ± 0.221 | 0.589 ± 0.211 | 0.427 ± 0.152 |

TABLE 8

Flies with ts8 Alleles. Blood uptake was greater for ts8 homozygous flies, p = 0.002
(ANOVA: F = 19.314, P = 0.002, n = 16).

| | Vaccine: OVA (Control) | Vaccine: TB8 | Vaccine: TS9 |
|---|---|---|---|
| 1 allele | n = 3 | n = 0 | n = 1 |
| | 0.331 ± 0.210 | | 0.007 |
| 2 alleles | n = 7 | n = 3 | n = 2 |
| | 1.023 ± 0.189 | 0.306 + 0.273 | 0.877 ± 0.035 |

TABLE 9

Flies with ts10 Alleles. Blood uptake was lower for homozygous ts10 flies fed on Control Cattle (ANOVA: F-4.190, p = 0.044, n = 86). Blood uptake was lower for homozygous ts10 flies fed on Control Cattle (ANOVA: F-4.190, p = 0.044, n = 86).

|           | Vaccine: OVA (Control) | Vaccine: TB8  | Vaccine: TS9  |
|-----------|------------------------|---------------|---------------|
| 1 allele  | n = 44                 | n = 41        | n = 34        |
|           | 0.998 ± 0.099          | 0.765 ± 0.113 | 0.975 ± 0.137 |
| 2 alleles | n-42                   | n = 31        | n = 23        |
|           | 0.682 ± 0.120          | 0.694 ± 0.099 | 0.869 ± 0.136 |

TABLE 10

Flies with ts10 alleles fed on control cattle.

|           | Feed Time 1   | Feed Time 2   | Feed Time 3   |
|-----------|---------------|---------------|---------------|
| 1 allele  | n = 10        | n = 25        | n = 9         |
|           | 0.864 ± 0.202 | 0.920 ± 0.238 | 1.365 ± 0.137 |
| 2 alleles | n = 17        | n = 17        | n = 8         |
|           | 0.409 ± 0.151 | 0.549 ± 0.103 | 1.550 ± 0.376 |

References Cited

Briegel, H., A. O. Lea, and M. J. Klowden. 1979. Hemoglobinometry as a method for measuring blood meal sizes of mosquitoes. J. Med. Entomol, 15:235-238.

Cupp, E. W., M. S. Cupp, J. M. C. Ribeiro, and S. E. Kunz. 1998. Blood-feeding strategy of *Haematobia irritans* (Diptera: Muscidae). J. Med. Entomol. 35:591-595.

Cupp, M. S., D. Zhang, and E. W. Cupp. 2000. Horn fly saliva targets thrombin action in hemostasis. J Med. Entomol. 37:416-421.

Cupp, M. S., E. W. Cupp, C. Navarre, N. Wisnewski, K. S. Brandt, G. M. Silver, D. Zhang, and V. Panangala. 2004. Evaluation of a recombinant salivary gland protein (thrombostasin) as a vaccine candidate to disrupt blood-feeding by horn flies. Vaccine. 22:2285-2297.

Cupp, M. S., E. W. Cupp, D. Zhang, X. Yue, L. Todd, V. Panangala, C. Navarre and E. Whitley. 2009. Salivary Gland Thrombostasin Isoforms Differentially Regulate Blood Uptake of Horn Flies Fed on New Zealand White Rabbits. J. Med. Entomol. 46(2):351-357.

Derouen, S. M., J. E. Miller, L. D. Foil, G. T. Gentry. 2009. Control of horn flies (*Haematobia irritans*) and gastrointestinal parasites and its relation with cow-calf performance. Vet, Parasitol. 162 (3-4):320-326.

Guglielinone, A. A., E. Gimeno, J. Idiart, W. F. Fisher, M. M. Volpogni, O. Qualm, O. S. Anziani, S. G. Flores, O. Warnke. 1999. Skin lesions and cattle hide damage from *Haematobia irritans* infestations. Med. Vet. Entomol. 13(3):324-329.

Hibler, C. P. 1966. Development of *Stephanofilaria stilesi* in the horn fly. J. Parasitol. 52(5):890-898.

Jensen, K.- M. V., J. B. Jespersen, M. A. Birkett, J. A. Pickett, G. Thomas, L. J. Wadhams and C. M. Woodcock. 2004. Variation in the load of the horn fly, *Haematobia irritans*, in cattle herds is determined by the presence or absence of individual heifers. Med. Vet. Entomol. 18:275-280.

Owens, W. E., S. P. Oliver, R E: Gillespie, C. H. Ray and S. C. Nickerson. 1998. Role of horn flies (*Haematobia irritans*) in *Staphylococcus aureus*-induced mastitis in dairy heifers. Am. J. Vet. Res. 59:1122-1124.

Owens, W. E., S. C. Nickerson and C. H. Ray. 2002. Effect of a pour-on and fly tag insecticide combination in controlling horn flies and *Staphylococcus aureus* mastitis in dairy heifers. 2002. J. Anim. Vet. Adv. 1(4):200-201.

Oyarzim, M. P., A. Quiroz and M. A. Birkett. 2008. Insecticide resistance in the horn fly: alternative control strategies. Med. Vet. Entomol. 22:188-202.

Pruett, J. H., C. D. Steelman, J. A. Miller, J. M. Pound and J. E. George. 2003. Distribution of horn flies on individual cows as a percentage of the total horn fly population. Vet. Parasitol. 116:251-258.

Sanson, D. W., A. A. DeRosa, G. R. Oremus and L. D. Foil. 2003. Effect of horn fly and internal parasite control on growth of beef heifers. Vet. Parasitol. 117(4):291-300.

Steelman, C. D. 1976. Effects of external and internal arthropod parasites on domestic livestock production. Annu. Rev. Entomol, 21:155-178.

Untalan, P. M., J. H. Pruett, H. N. Atteberry, and C. D. Steelman. 2006. Thrombostasin isoform frequency in a Central Texas field population of the Horn Fly, *Haematobia irritans*. Vet. Parasitol. 142:359-366.

Zhang, D., M. S. Cupp, and E. W. Cupp. 2001. Polymorphism of Thrombostasin revealed in cDNA library and genomic DNA. Mol. Gen. Genom. 266:296-302.

Zhang, D., M. S. Cupp, and E. W. Cupp. 2002. Thrombostasin: Purification, molecular cloning, and expression of a novel antithrombin protein from horn fly saliva. Insect Biochem. Mal. Biol. 32:321-330.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

All patents and publications cited in this specification are hereby incorporated by reference thereto in their entirety.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

It should also be understood that, unless clearly indicated to the contrary, in any methods claimed herein that include more than one act, the order of the acts of the method is not necessarily limited to the order in which the acts of the method are recited, but the invention includes embodiments in which the order is so limited. Furthermore, where the claims recite a composition, the invention encompasses methods of using the composition and methods of making the composition. Where the claims recite a composition, it should be understood that the invention encompasses methods of using the composition and methods of making the composition.

What is claimed is:

1. A vaccine composition consisting of
   a. a combination of an isolated thrombostasin peptide or protein consisting of an isolated thrombostasin peptide or protein comprising SEQ ID NO 3 and an isolated thrombostasin peptide or protein comprising SEQ ID NO 5; and
   b. an adjuvant in an amount sufficient to enhance antigenicity of said combination;
   c. optionally, one or more agents selected from the group consisting of a preservative, an isotonicity additive, phosphate buffered saline, a stabilizer, a vasoconstriction agent, a dispersing agent, a thickening agent, an anticaking agent, a pharmaceutically acceptable excipient, and combinations thereof;
      wherein said composition is capable of generating an immune response in a mammal to a horn fly thrombostasin protein; and
      wherein said mammal is *B. Taurus*.

2. The composition of claim 1 wherein said isolated thrombostasin peptide or protein comprising SEQ ID NO 3 and/or said isolated thrombostasin peptide or protein comprising SEQ ID NO 5 further comprises an immunogenic sequence comprising amino acids, wherein said immunogenic sequence is operatively connected to said peptide or protein.

3. The composition of claim 2, wherein said immunogenic sequence is from about 10 to about 500 amino acids.

4. A vaccine composition consisting of
   a. a combination of isolated thrombostasin peptide or protein consisting of an isolated thrombostasin peptide or protein comprising SEQ ID NO 8 and an isolated thrombostasin peptide or protein comprising SEQ ID NO 10; and
   b. an adjuvant in an amount sufficient to enhance antigenicity of said combination;
   c. optionally, one or more agents selected from the group consisting of a preservative, an isotonicity additive, phosphate buffered saline, a stabilizer, a vasoconstriction agent, a dispersing agent, a thickening agent, an anticaking agent, a pharmaceutically acceptable excipient, and combinations thereof;
      wherein said composition is capable of generating an immune response in a mammal to a horn fly thrombostasin protein; and
      wherein said mammal is *B. Taurus*.

5. The composition of claim 4, wherein said isolated thrombostasin peptide or protein comprising SEQ ID NO 8 and/or said isolated thrombostasin peptide or protein comprising SEQ ID NO 10 further comprises an immunogenic sequence comprising amino acids, wherein said immunogenic sequence is operatively connected to said peptide or protein.

6. The composition of claim 5, wherein said immunogenic sequence is from about 10 to about 500 amino acids.

7. A method for decreasing blood uptake from a mammal by *Haematobia irritans*, comprising the step of vaccinating said mammal with a composition selected from the group consisting of the composition of claim 1, the composition of claim 4, and combinations thereof.

8. The method of claim 7, wherein said vaccination step comprises more than one administration of said composition.

9. The method of claim 7, wherein said vaccination step occurs intradermally, parenterally, orally, intranasally, oronasally, or transdermally.

10. The method of claim 7, wherein said mammal is vaccinated at a plurality of injection sites.

11. The method of claim 7, wherein said mammal is vaccinated a plurality of times.

12. The method of claim 7, wherein said vaccination step occurs prophylactically.

13. The method of claim 7, wherein said vaccination step occurs therapeutically.

14. The method of claim 7, wherein said mammal is *B. Taurus*.

15. The method of claim 7, wherein said vaccination step occurs intradermally.

16. A method for decreasing blood uptake from a mammal by *Haematobia irritans*, comprising the step of vaccinating said mammal with the composition of claim 4.

* * * * *

SEQUENCE LISTING

<160> NUMBER OF SEQ ID NOS: 14

<210> SEQ ID NO 1
<211> LENGTH: 157
<212> TYPE: PRT
<213> ORGANISM: Haematobia irritans

<400> SEQUENCE: 1

Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Gly Gln Trp Ala Pro Leu Asp
        35                  40                  45

Phe Asp Tyr Asn Ser Leu Pro Gly Leu Ser Gly Tyr Asn His Glu Gln
    50                  55                  60

Gln Asp Tyr Glu Glu Asp Ser Tyr Arg His Val Arg Ser Ala Gly Pro
65                  70                  75                  80

Ile Thr Leu Gln Leu Asn Asp Asp Asp Asp Ser Gly Ile Pro
                85                  90                  95

Ile Phe Glu Met Asp Asp Glu Asp Glu Asp Ser Asn Asp Asn Gln Lys
                100                 105                 110

Phe Pro Leu Ser Phe Glu Arg Phe Pro Glu Asn Glu Lys Asn Gln Glu
            115                 120                 125

Gly Leu Arg Ala Arg Phe Asn Lys Phe Met Ala Lys Phe Thr Ser Leu
        130                 135                 140

Phe Gly Arg Arg Arg Gly Val Asp Val Pro Asn Ala Ala
145                 150                 155

<210> SEQ ID NO 2
<211> LENGTH: 157
<212> TYPE: PRT
<213> ORGANISM: Haematobia irritans

<400> SEQUENCE: 2

Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Gly Gln Trp Ala Pro Leu Asp
        35                  40                  45

Phe Asp Tyr Asn Ser Leu Pro Gly Leu Ser Gly Tyr Asn His Glu Gln
    50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Asp Ser Gly Ile Pro
                85                  90                  95

Ile Phe Glu Met Asp Asp Glu Asp Glu Asp Ser Asn Asp Asn Gln Lys
                100                 105                 110

Phe Pro Leu Ser Phe Glu Arg Phe Pro Glu Asn Glu Lys Asn Gln Glu
            115                 120                 125

Gly Leu Arg Ala Arg Phe Asn Lys Phe Met Ala Lys Phe Thr Ser Leu
        130                 135                 140

Phe Gly Arg Arg Arg Ser Val Asp Val Pro Asn Ala Ala
145                 150                 155

<210> SEQ ID NO 3
<211> LENGTH: 157
<212> TYPE: PRT
<213> ORGANISM: Haematobia irritans

<400> SEQUENCE: 3

Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Ser Gly Gln Trp Ala Pro Leu Asp
        35                  40                  45

Phe Asp Tyr Asn Ser Leu Pro Gly Leu Ser Gly Tyr Asn His Glu Gln
    50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Asp Ser Gly Ile Pro
                85                  90                  95

Ile Phe Glu Met Asp Asp Glu Asp Glu Asp Ser Asn Asp Asn Gln Lys
            100                 105                 110

Phe Pro Leu Ser Phe Glu Arg Phe Pro Glu Asn Glu Lys Asn Gln Glu
        115                 120                 125

Gly Leu Arg Ala Arg Phe Asn Lys Phe Met Ala Lys Phe Thr Ser Leu
    130                 135                 140

Phe Gly Arg Arg Arg Gly Val Asp Val Pro Asn Ala Ala
145                 150                 155

<210> SEQ ID NO 4
<211> LENGTH: 157
<212> TYPE: PRT
<213> ORGANISM: Haematobia irritans

<400> SEQUENCE: 4

Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Ser Gly Gln Trp Ala Pro Leu Asp
        35                  40                  45

Phe Asp Tyr Asn Ser Leu Pro Gly Leu Ser Gly Tyr Asn His Glu Gln
    50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Asp Ser Gly Ile Pro
                85                  90                  95

Ile Phe Glu Met Asp Asp Glu Asp Glu Asp Ser Asn Asp Asn Gln Lys
            100                 105                 110

Phe Pro Leu Ser Phe Glu Arg Phe Pro Glu Asn Glu Lys Asn Gln Val
        115                 120                 125

Gly Leu Arg Ala Arg Phe Asn Lys Phe Met Ala Lys Phe Thr Ser Leu
    130                 135                 140

Phe Gly Arg Arg Arg Gly Val Asn Val Pro Asn Ala Ala
145                 150                 155

<210> SEQ ID NO 5
<211> LENGTH: 157
<212> TYPE: PRT

<213> ORGANISM: Haematobia irritans

<400> SEQUENCE: 5

Gln Asn Leu Val Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Gly Gln Trp Ala Pro Leu Asp
        35                  40                  45

Phe Asp Tyr Asn Ser Leu Pro Gly Leu Ser Tyr Asn His Glu Gln
 50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Ser Gly Ile Pro
                85                  90                  95

Ile Phe Glu Met Asp Asp Glu Asp Val Asp Ser Asn Asp Asn Gln Lys
                100                 105                 110

Phe Pro Leu Ser Phe Glu Arg Phe Pro Glu Asn Glu Lys Asn Gln Val
            115                 120                 125

Gly Leu Arg Ala Arg Phe Asn Lys Phe Met Ala Lys Phe Thr Ser Leu
        130                 135                 140

Phe Gly Arg Arg Arg Gly Val Asn Val Pro Asn Ala Ala
145                 150                 155

<210> SEQ ID NO 6
<211> LENGTH: 81
<212> TYPE: PRT
<213> ORGANISM: Haematobia irritans

<400> SEQUENCE: 6

Ser Ala Gly Pro Ile Thr Leu Gln Leu Asn Asp Asp Asp Asp Asp Asp
1               5                   10                  15

Ser Gly Ile Pro Ile Phe Glu Met Asp Asp Glu Asp Glu Asp Ser Asn
            20                  25                  30

Asp Asn Gln Lys Phe Pro Leu Ser Phe Glu Arg Phe Pro Glu Asn Glu
        35                  40                  45

Lys Asn Gln Glu Gly Leu Arg Ala Arg Phe Asn Lys Phe Met Ala Lys
    50                  55                  60

Phe Thr Ser Leu Phe Gly Arg Arg Arg Gly Val Asp Val Pro Asn Ala
65                  70                  75                  80

Ala

<210> SEQ ID NO 7
<211> LENGTH: 81
<212> TYPE: PRT
<213> ORGANISM: Haematobia irritans

<400> SEQUENCE: 7

Ser Ala Gly Pro Ile Thr Leu Gln Leu Asp Asp Asp Asp Asp Asp
1               5                   10                  15

Ser Gly Ile Pro Ile Phe Glu Met Asp Asp Glu Asp Glu Asp Ser Asn
            20                  25                  30

Asp Asn Gln Lys Phe Pro Leu Ser Phe Glu Arg Phe Pro Glu Asn Glu
        35                  40                  45

Lys Asn Gln Glu Gly Leu Arg Ala Arg Phe Asn Lys Phe Met Ala Lys
    50                  55                  60

```
Phe Thr Ser Leu Phe Gly Arg Arg Arg Ser Val Asp Val Pro Asn Ala
 65                  70                  75                  80

Ala
```

<210> SEQ ID NO 8
<211> LENGTH: 81
<212> TYPE: PRT
<213> ORGANISM: Haematobia irritans

<400> SEQUENCE: 8

```
Ser Ala Gly Pro Ile Thr Leu Gln Leu Asp Asp Asp Asp Asp Asp Asp
  1               5                  10                  15

Ser Gly Ile Pro Ile Phe Glu Met Asp Asp Glu Asp Glu Asp Ser Asn
                 20                  25                  30

Asp Asn Gln Lys Phe Pro Leu Ser Phe Glu Arg Phe Pro Glu Asn Glu
             35                  40                  45

Lys Asn Gln Glu Gly Leu Arg Ala Arg Phe Asn Lys Phe Met Ala Lys
         50                  55                  60

Phe Thr Ser Leu Phe Gly Arg Arg Arg Gly Val Asp Val Pro Asn Ala
 65                  70                  75                  80

Ala
```

<210> SEQ ID NO 9
<211> LENGTH: 81
<212> TYPE: PRT
<213> ORGANISM: Haematobia irritans

<400> SEQUENCE: 9

```
Ser Ala Gly Pro Ile Thr Leu Gln Leu Asp Asp Asp Asp Asp Asp Asp
  1               5                  10                  15

Ser Gly Ile Pro Ile Phe Glu Met Asp Asp Glu Asp Glu Asp Ser Asn
                 20                  25                  30

Asp Asn Gln Lys Phe Pro Leu Ser Phe Glu Arg Phe Pro Glu Asn Glu
             35                  40                  45

Lys Asn Gln Val Gly Leu Arg Ala Arg Phe Asn Lys Phe Met Ala Lys
         50                  55                  60

Phe Thr Ser Leu Phe Gly Arg Arg Arg Gly Val Asn Val Pro Asn Ala
 65                  70                  75                  80

Ala
```

<210> SEQ ID NO 10
<211> LENGTH: 81
<212> TYPE: PRT
<213> ORGANISM: Haematobia irritans

<400> SEQUENCE: 10

```
Ser Ala Gly Pro Ile Thr Leu Gln Leu Asp Asp Asp Asp Asp Asp Asp
  1               5                  10                  15

Ser Gly Ile Pro Ile Phe Glu Met Asp Asp Glu Asp Val Asp Ser Asn
                 20                  25                  30

Asp Asn Gln Lys Phe Pro Leu Ser Phe Glu Arg Phe Pro Glu Asn Glu
             35                  40                  45

Lys Asn Gln Val Gly Leu Arg Ala Arg Phe Asn Lys Phe Met Ala Lys
         50                  55                  60

Phe Thr Ser Leu Phe Gly Arg Arg Arg Gly Val Asn Val Pro Asn Ala
 65                  70                  75                  80

Ala
```

```
<210> SEQ ID NO 11
<211> LENGTH: 189
<212> TYPE: PRT
<213> ORGANISM: Haematobia irritans

<400> SEQUENCE: 11

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Gln Asn Leu Val Ser Gly Arg Arg Gln His Gly Ala Gln Gly Leu Ser
        35                  40                  45

Gly Tyr Ser Gly Asp Asn Asp Trp Gly Tyr Tyr Gly Glu Ala Gly Ala
    50                  55                  60

Pro Gly Ser Asp Tyr Ser Gly Ser Ser Gly Gln Trp Ala Pro Leu Asp
65                  70                  75                  80

Phe Asp Tyr Asn Ser Leu Pro Gly Leu Ser Gly Tyr Asn His Glu Gln
                85                  90                  95

Gln Asp Tyr Glu Glu Asp Ser Tyr Arg His Val Arg Ser Ala Gly Pro
            100                 105                 110

Ile Thr Leu Gln Leu Asp Asp Asp Asp Asp Asp Ser Gly Ile Pro
        115                 120                 125

Ile Phe Glu Met Asp Asp Glu Asp Val Asp Ser Asn Asp Asn Gln Lys
    130                 135                 140

Phe Pro Leu Ser Phe Glu Arg Phe Pro Glu Asn Glu Lys Asn Gln Val
145                 150                 155                 160

Gly Leu Arg Ala Arg Phe Asn Lys Phe Met Ala Lys Phe Thr Ser Leu
                165                 170                 175

Phe Gly Arg Arg Arg Gly Val Asn Val Pro Asn Ala Ala
            180                 185

<210> SEQ ID NO 12
<211> LENGTH: 187
<212> TYPE: PRT
<213> ORGANISM: Haematobia irritans

<400> SEQUENCE: 12

Met Ala Gln Asn Val Leu Ser Gly Arg Arg Gln His Gly Ala Gln Gly
1               5                   10                  15

Leu Ser Gly Tyr Ser Gly Asp Asn Asp Trp Gly Tyr Tyr Gly Glu Ala
            20                  25                  30

Gly Ala Pro Gly Ser Asp Tyr Ser Gly Ser Ser Gly Gln Trp Ala Pro
        35                  40                  45

Leu Asp Phe Asp Tyr Asn Ser Leu Pro Gly Leu Ser Gly Tyr Asn His
    50                  55                  60

Glu Gln Gln Asp Tyr Glu Glu Asp Ser Tyr Arg His Val Arg Ser Ala
65                  70                  75                  80

Gly Pro Ile Thr Leu Gln Leu Asp Asp Asp Asp Asp Asp Ser Gly
                85                  90                  95

Ile Pro Ile Phe Glu Met Asp Asp Glu Asp Asp Ser Asn Asp Asn
            100                 105                 110

Gln Lys Phe Pro Leu Ser Phe Glu Arg Phe Pro Glu Asn Glu Lys Asn
        115                 120                 125

Gln Glu Gly Leu Arg Ala Arg Phe Asn Lys Phe Met Ala Lys Phe Thr
    130                 135                 140
```

```
Ser Leu Phe Gly Arg Arg Arg Gly Val Asp Val Pro Asn Ala Ala Gln
145                 150                 155                 160

Leu Tyr Thr Arg Ala Ser Gln Pro Glu Leu Ala Pro Glu Asp Pro Glu
                165                 170                 175

Asp Leu Glu His His His His His His
            180                 185

<210> SEQ ID NO 13
<211> LENGTH: 19
<212> TYPE: DNA
<213> ORGANISM: artificial
<220> FEATURE:
<223> OTHER INFORMATION: Primer

<400> SEQUENCE: 13
atcatgaagc atttcgtag                                          19

<210> SEQ ID NO 14
<211> LENGTH: 21
<212> TYPE: DNA
<213> ORGANISM: artificial
<220> FEATURE:
<223> OTHER INFORMATION: Primer

<400> SEQUENCE: 14
gcttatgcag cattgggaac a                                       21
```